(12) United States Patent
He et al.

(10) Patent No.: US 7,572,577 B2
(45) Date of Patent: Aug. 11, 2009

(54) METHODS FOR RECOVERY OF DNA FROM MRNA IN RIBOSOME DISPLAY COMPLEXES

(75) Inventors: Mingyue He, Cambridge (GB); Alison M. Jackson, Cambridge (GB)

(73) Assignee: Crescendo Biologics Limited, Cambridge (GB)

( * ) Notice: Subject to any disclaimer, the term of this patent is extended or adjusted under 35 U.S.C. 154(b) by 338 days.

(21) Appl. No.: 10/549,778

(22) PCT Filed: Mar. 19, 2004

(86) PCT No.: PCT/GB2004/001211

§ 371 (c)(1), (2), (4) Date: Aug. 21, 2006

(87) PCT Pub. No.: WO2004/083461

PCT Pub. Date: Sep. 30, 2004

(65) Prior Publication Data

US 2006/0281086 A1 Dec. 14, 2006

(30) Foreign Application Priority Data

Mar. 19, 2003 (GB) .................................. 0306305.4
May 16, 2003 (GB) .................................. 0311351.1

(51) Int. Cl.
*C12Q 1/68* (2006.01)
*C12P 19/34* (2006.01)

(52) U.S. Cl. .......................................... 435/6; 435/91.2

(58) Field of Classification Search .................... 435/6, 435/91.2
See application file for complete search history.

(56) References Cited

U.S. PATENT DOCUMENTS 6,291,170 B1 9/2001 Van Gelder et al.
6,379,932 B1 4/2002 Arnold et al.

FOREIGN PATENT DOCUMENTS

EP 0 549 107 A 6/1993
WO 01/38556 A1 5/2001

OTHER PUBLICATIONS

He et al., Journal of Immunological Methods 231, 105-117 (1999).*
Bieberich et al., Analytical Biochemistry 287, 294-298 (2000).*

(Continued)

*Primary Examiner*—Kenneth R. Horlick
(74) *Attorney, Agent, or Firm*—Goodwin Procter LLP

(57) ABSTRACT

The invention provides a method for recovery of cDNA from mRNA, comprising reverse transcription (RT) of mRNA using a RT primer which includes a sequence based on the 5' consensus region of the mRNA which is identical or similar to 5' consensus region of the mRNA and which includes a sequence capable of specifically hybridising to the 3' region of the mRNA, followed by polymerase chain reaction (PCR) using a single primer to generate ss cDNA, ds cDNA and amplify the cDNA. Primers for use in methods of the invention and kits for performing methods of the invention are also provided. The methods of the invention can partially or fully automated.

10 Claims, 9 Drawing Sheets

OTHER PUBLICATIONS

Dixon et al. (Oct. 1998) "Expression profiling of single cells using 3 prime end amplification (TPEA) PCR" Nucleic Acids Research 26: 4426-31.

He et al. (Jul. 2002) "Ribosome Display: Cell-free protein display technology" Briefings in Functional Genomics and Proteomics 1: 204-12.

International Search Report, Transmittal for Written Opinion of the International Searching Authority, and Written Opinion of the International Searching Authority for International Patent Application Serial No. PCT/GB2004/001211, dated Aug. 17, 2004, 11 pages.

United Kingdom Patent Office Search Report for Patent Application Serial No. 0306305, dated Aug. 12, 2003, 1 page.

* cited by examiner

(a) 'Single primer' PCR

(b) Fingerprinting (a) Diagram showing ARM complex (b) Gel analysis of RT-PCR product 0: Primer 0   C: Solution Control
1: Primer 1   P: PCR control
2: Primer 2   RT: RT-PCR

35 cycles of single primer PCR

Marker　NC　1　2　1　2
　　　　　　└─┘└─┘
　　　　　　42°C　65°C

NC: negative control
1. 0.5ul cDNA template;
2. 1ul cDNA template

METHODS FOR RECOVERY OF DNA FROM MRNA IN RIBOSOME DISPLAY COMPLEXES

CROSS-REFERENCE TO RELATED APPLICATIONS

This application is the national stage of International (PCT) Patent Application Serial No. PCT/GB2004/001211, filed Mar. 19, 2004, and published under PCT Article 21(2) in English, which claims the benefit of and priority to Great Britain Patent Application Serial No. 0306305.4, filed Mar. 19, 2003, and Great Britain Patent Application Serial No. 0311351.1, filed May 16, 2003. The entire disclosure of International Patent Application Serial No. PCT/GB2004/001211 is incorporated by reference herein for all purposes.

TECHNICAL FIELD

The present invention relates to the recovery of DNA, and more particularly it relates to a highly sensitive method for the generation and recovery of cDNA and to primers suitable for use in such methods.

BACKGROUND TO THE INVENTION

The Polymerase Chain Reaction (PCR) amplifies DNA sequences through repeated cycles of template denaturation, primer annealing and elongation. Reverse transcription (RT) coupled with PCR (RT-PCR) combines cDNA synthesis from mRNA templates with PCR amplification to provide a rapid and sensitive method for detection, conversion and recovery of mRNA as DNA. The RT-PCR process can be performed in either one-tube or two-tube formats. In one-tube RT-PCR, the RT and PCR take place successively in a single tube using a mutual buffer for both reactions. In two-tube RT-PCR, RT and PCR are carried out separately. It has been shown that one-tube RT-PCR has the greater sensitivity and that as little as 100 copies of mRNA can be amplified (#TB220, Promega). In two tube RT-PCR, each step can be optimised separately and it may produce higher yields of DNA in some circumstances (TechNotes 9[6], Ambion).

High sensitivity (i.e. obtaining sufficient amount of DNA from as little template as possible) and high specificity (i.e. amplifying only the desired template) are key to successful PCR. They are affected by many factors including the choice of appropriate DNA polymerases, design of suitable primers, suitable buffers, thermal cycling parameters and also the quality of templates.

A single primer PCR approach has been developed for cloning unknown DNA sequences (Hermann et al., (2000) BioTechniques 29: 1176-1180) and elimination of primer-dimer accumulation in PCR (Brownie et al., (1997) Nucleic Acids Res. 25: 3235-3241). The single primer PCR uses one primer in the PCR mixture to amplify DNA having identical flanking sequences at both ends. Recently, this approach has been used to amplify single molecules of double-stranded DNA through 80 PCR cycles, a method termed single-molecule PCR (SM-PCR) (Rungpragayphan et al., (2002) J. Mol. Biol. 318: 395-405). In this method, double-stranded DNA is first amplified by PCR using two primers to introduce a tag sequence at both ends, after which the modified DNA is diluted and used as the template for SM-PCR (Rungpragayphan et al., (2002) J. Mol. Biol. 318: 395-405). However, none of these methods provided a sensitive procedure for cDNA recovery from mRNA A number of display technologies have been developed for selection of proteins. Using the principle of coupling phenotype (protein) to genotype (gene), proteins have been successfully displayed on phage, cell surface and virus or ribosome, plasmid and mRNA. Prokaryotic and eukaryotic ribosome display systems have been used for selection of peptides, single-chain antibodies, enzymes, stable protein scaffolds and other ligand-binding domains. Display technology recovers DNA through the functionality of the encoded protein. A review of ribosome display technology is provided by He & Taussig (2002) *Briefings in Functional Genomics and Proteomics*, 1(2): 204-212.

Sensitive DNA recovery from mRNA is required in ribosome display. This cell-free protein display method allows the selection and evolution of proteins in vitro (He and Taussig (1997) Nucleic Acids Res. 25: 5153-5134; Hanes and Pluckthun, (1997) Proc. Natl. Acad. Sci. USA 94: 4937-4942). The method generates a library of ribosome display complexes, which are protein-ribosome-mRNA (PRM) complexes, from a diversity of DNA molecules by cell free expression, followed by capture of specific PRM complexes with a ligand through binding interaction of the displayed nascent protein. The associated mRNA is then retrieved and amplified as cDNA by RT-PCR. A key step in ribosome display is the efficient recovery of genetic material from PRM complexes after selection. A highly sensitive recovery method would allow rare species to be isolated from very large libraries. Currently, two principal recovery methods are employed. One is a ribosome disruption procedure used in prokaryotic ribosome display, which releases mRNA by the dissociation of ribosome complexes with EDTA followed by RT-PCR (Hanes and Pluckthun, 1997). The other method is an in situ RT-PCR method used in eukaryotic ribosome display (He and Taussig, 1997), which recovers DNA directly from PRM complexes without ribosome disruption through the use of a primer hybridising at least 60 nucleotides upstream of the 3' end of the mRNA in order to avoid the region occupied by stalling ribosome. It has been demonstrated that the in situ RT-PCR procedure is more effective for recovery of DNA from eukaryotic ribosome complexes than the prokaryotic ribosome disruption method (He and Taussig, 2002 Briefings Func Genomics & Proteomics 1: 204-212). However, both methods require a sensitive procedure to recover cDNA from mRNA.

Sensitive recovery of low levels of mRNA would also be extremely useful in techniques such as single cell RT-PCR where for example, gene expression patterns are to be studied. Many cellular genes are expressed at very low levels. These are hard or even impossible to recover by traditional RT-PCR methods. Currently, repeated rounds of PCR reactions are usually performed (Gaynor et al., (1996) Biotechniques 21: 286-291). This can lead to artificial errors and meticulous controls are required. The RT-PCR method described here is sensitive enough such that only a single PCR reaction procedure is required, even when only a single cDNA molecule or a small number of DNA molecules is present as the initial PCR template.

STATEMENT OF INVENTION

The present invention provides a primer designed for use with a given mRNA, the primer comprising, i.e. including or consisting of, a 5' sequence based on a 5' region of the mRNA and a 3' sequence which hybridises to a 3' region of the mRNA.

The invention provides a primer designed for use with mRNA comprising a 5' sequence based on a 5' consensus region of the mRNA and a 3' sequence capable of hybridising to a 3' region of the mRNA.

A primer designed for use with mRNA is referred to herein as a reverse transcription (RT) primer.

Preferably, in a RT primer according to the invention, the primer 5' sequence comprises sequence identical or similar to sequence of the mRNA 5' consensus region. Preferably, the RT primer 5' sequence is identical or similar to sequence of the mRNA 5' region.

Preferably in a RT primer according to the invention, the primer 3' sequence comprises sequence complementary to the mRNA 3' region. Preferably, the primer 3' sequence is complementary to the mRNA 3' region.

According to the present invention, an RT primer for use with mRNA comprises a 5' flanking sequence and a 3' hybridising sequence.

The flanking sequence is designed from a knowledge of the 5' region of the mRNA, and is a sequence which will hybridise specifically with DNA complementary to a part of the mRNA 5' region under the conditions in which the RT reaction is performed. Typically the flanking region is identical to a part of the mRNA 5' region or is similar to a part of the mRNA 5' region, by "similar" it is meant that the sequence is not identical, but has a high degree of homology to the mRNA 5' region (e.g. 80 to 99% homology, preferably 85 to 99% homology, more preferably 90 to 99% homology, yet further preferably 95 to 99% homology to the mRNA 5'region). Identical and similar sequences are able to hybridise specifically with DNA complementary to a part of the mRNA 5' region under the conditions in which the RT reaction is performed as described herein, optionally with pre-heating step. The flanking region is usually in the range of an 8-mer to a 30-mer, such as a 10-mer to a 20-mer, preferably around a 15-mer.

The hybridising sequence is designed from a knowledge of the 3' region of the mRNA and is capable of hybridising specifically to a part of the mRNA 3' region. Typically the hybridising sequence is identical or similar to a sequence complementary to a part of the mRNA 3' region. By "similar" it is meant that the sequence is degenerate, i.e. does not exactly correspond to the sequence complementary to a part of the mRNA 3'region; identical and similar sequences are capable of specific hybridisation to a sequence complementary to a part of the mRNA 3'region. A "similar" sequence has a high degree of homology to a sequence complementary to a part of the 3' region of the mRNA (e.g. 80 to 99% homology, preferably 85 to 99% homology, more preferably 90 to 99% homology, yet further preferably 95 to 99% homology to a sequence complementary to a part of the 3' region of the mRNA). A "similar" sequence is capable of specific hybridisation to DNA complementary to a part of the mRNA 3'region under conditions in which the RT reaction is performed as described herein, optionally with pre-heating step, and/or under conditions in which a PCR reaction is performed as described herein. The hybridising sequence is usually in the range of an 8-mer to a 30-mer, such as a 10-mer to a 20-mer, preferably around a 15-mer. In the primer, the hybridising sequence is 3' relative to the flanking sequence.

The present invention further provides a method for generating a cDNA molecule which comprises reverse transcription of mRNA using a primer (RT primer) according to the invention. Also provided is a method for recovery of double stranded cDNA which comprises generating single stranded cDNA by reverse transcription of mRNA using a RT primer according to the invention (forming an mRNA/ss cDNA duplex), and PCR to generate and amplify ds cDNA using a single PCR primer; preferably the single primer comprises (i.e. is or includes) a sequence based on the mRNA 5' consensus region, i.e. a flanking sequence as described above.

Thus the present invention provides an ultra-sensitive RT-PCR procedure which is generally applicable to generate and recover ds cDNA from mRNA. The high sensitivity and specificity of this method is made possible by the novel design of an RT primer to introduce a flanking sequence into single-stranded cDNA which can then be used as a template for the subsequent amplification to be carried out by single primer PCR, using a primer that anneals at the flanking sequence. This differs substantially from previous single primer PCR methods. Earlier methods did not indicate how DNA would be recovered from mRNA. In contrast, the present invention uses mRNA as the template. The flanking sequence is designed from the 5' consensus region of the mRNA rather than an artificially designed sequence and is introduced into single stranded cDNA rather than double stranded DNA.

The present invention yet further comprises a method for recovery of cDNA from mRNA, said method comprising:

(a) reverse transcription (RT) using a RT primer according to the invention which comprises a sequence identical or similar to the 5' consensus region of the mRNA and a sequence capable of specifically hybridising to a 3' region of the mRNA, followed by, (b) polymerase chain reaction (PCR) using a single PCR primer according to the invention to amplify cDNA.

In one aspect of a method for recovery of DNA according to the invention, the ss DNA template for the PCR reaction can present as a mixture of a small number of molecules or as a single molecule. This can be achieved prior to the PCR reaction by separation of the ss cDNA molecules produced in the RT step. Separation can be performed by dilution e.g. serial dilution of the of the RT reaction product, and/or by an electrophoretic method or a biochemical method such as primer hybridisation.

In methods of the invention that include recovery of cDNA, it is preferred that the mRNA is first at least partially denatured before the RT reaction, e.g. by heat treatment or a chemical method. This reduces secondary structure in the mRNA and allows the primer to access its target sequence. Preferably the sample containing mRNA is heated to a temperature in the range of from 40° C. to 75° C., preferably to a temperature in the range of from 42° C. to 70° C., more preferably to 65° C. or higher. Suitable the heat treatment is applied for 2 to 20 minutes, preferably 3 to 10 minutes, most preferably about 5 minutes. In methods involving recovery of cDNA from ribosome display complexes, (protein-mRNA-complexes, such as antibody-ribosome-mRNA complexes) this treatment step is optimised, e.g. temperature and reaction conditions are chosen, to maintain association of the ribosome with the mRNA. Suitable temperature conditions that maintain integrity of protein-mRNA complexes are by heating to a temperature in the range of 40° C. to 70° C., preferably 42° C. to 65° C. for 2 to 10 minutes, preferably for around 5 minutes.

The invention also provides a method for recovery of DNA fragments from mRNA, said method comprising:

(a) heating of mRNA sample, followed by, (b) RT using a primer which includes a sequence identical to or similar to the sequence at the 5' consensus region of the mRNA, followed by (c) PCR using a single primer to amplify the cDNA.

In one aspect of a method for recovery of DNA according to the invention, the ss DNA template for the PCR reaction can present as a mixture of a small number of molecules or as a single molecule. Thus the invention provides method for recovery of DNA fragments from mRNA, said method comprising (a) heating of mRNA sample, followed by, (b) RT using a RT primer according to the invention which includes a sequence identical to or similar to the sequence at the 5' consensus region of the mRNA, followed by, (c) PCR using a single PCR primer according to the invention to amplify the cDNA either as mixture or a single molecule.

In a method of the invention for recovery of DNA fragments, the RT primer used is suitably any oligonucleotide or mixture of oligonucleotides in which a 3' primer region is complementary to a 3' region of the template mRNA and in which the 5'region has a sequence identical or similar to the 5' region of the mRNA. Preferably, the RT primer is any oligonucleotide or mixture of oligonucleotides in which a 3' primer region is complementary to a 3' region of the template mRNA including (but not exclusively) the poly A tail, i.e. the 3' primer region may optionally be complementary to a region which includes at least part of the poly A tail and in which the 5' primer region has a sequence similar or identical to the 5' region of the mRNA.

Preferably the RT primer used is any oligonucleotide or mixture of oligonucleotides in which a 3' primer region is complementary to a 3' region of the template mRNA and in which the 5' primer region has a sequence similar or identical to the 5' region of the mRNA including the transcriptional start site, regulatory elements, kozak sequence, translational start codon, any part of the translated sequence or any family specific consensus sequence found in the 5' region.

More preferably the RT primer used is any oligonucleotide or mixture of oligonucleotides in which a 3' primer region is complementary to a 3' region of the template mRNA including (but not exclusively) the poly A tail, and in which the 5' primer region has a sequence similar or identical to the 5' region of the mRNA including the transcriptional start site, regulatory elements, kozak sequence, translational start codon, any part of the translated sequence or any family specific consensus sequence found in the 5' region.

In a preferred method that includes a PCR step, the single PCR primer used for PCR is identical, overlapping with or similar to, the 5' region sequence of the RT primer used for reverse transcription.

Also provided is a method for RT-PCR recovery of cDNA from mRNA in ribosome display complexes, said method comprising:

(a) RT using a primer comprising a 5' primer region sequence which is similar or identical to the 5' consensus region of mRNA and a 3' primer region sequence complementary to a 3' region of mRNA, followed by, (b) PCR using a single primer to amplify cDNA.

The 3' primer region of an RT primer according to the invention can be complementary to a 3' region of the template mRNA including the poly A tail, i.e. the 3' primer region may optionally be complementary to a region which includes at least part of the poly A tail.

One particular application of the invention is recovery of cDNA from protein-mRNA display complexes such as ribosome display complexes. In this application, RT and PCR are carried out separately in a two-step format and each step is optimised to improve the sensitivity and specificity of DNA recovery.

Ribosome display is an in vitro protein display system which links proteins to the mRNA that encodes them, so selection of a protein (e.g. by binding to a ligand) simultaneously captures the mRNA that encodes the protein. The link between protein and mRNA in ribosome display complexes is produced by in vitro translation of mRNA to provide protein-ribosome-mRNA (PRM) complexes. The captured mRNA can then be reverse transcribed into single stranded cDNA which can be converted to ds DNA and amplified by PCR, providing the gene encoding the selected protein. The RT reaction can be performed on mRNA in the display complex, or the mRNA can be isolated from the display complex then used in the RT step. Suitable methods for disruption/dissociation of ribosome complexes are known in the art and include EDTA treatment and/or phenol extraction.

In ribosome display, PRM complexes are produced by ribosome stalling such that the nascent protein and mRNA remain associated. Strategies to achieve this include the addition of antibiotics such as rifampicin or chloramphenicol (for prokaryotic ribosomes), or such as cyclohexaminde (for eukaryotic ribsomes) to halt translation at random. Alternatively, the ribosome may be caused to stall at the 3' end of the mRNA template because of deletion of the stop codon from the mRNA template; the stop codon which is normally being recognised by release factors that trigger detachment of the nascent polypeptide.

In general, ribosome display constructs should contain a promoter (T7, SP6 or T3) and a translation initiation signal such as a Shine-Dalgarno (prokaryotic) or Kozak (eukaryotic) sequence. A consensus sequence for protein initiation in both *E. coil* and eukaryotic systems has also been described. To enable the complete nascent protein to be displayed and fold into its active conformation, a spacer domain of at least 23-30 amino acids' length is required at the C terminus, to allow the protein to exit completely from the ribosome 'tunnel'. The spacer also provides a known sequence for the design of primers for RT-PCR recovery. A number of different spacers have been successfully used, including the constant region of immunoglobulin kappa chain (Cκ), gene III of filamentous phage M13 and the $C_H3$ domain of human IgM. Spacer length has been shown to affect display efficiency: a spacer of 116 amino acids was more efficient in displaying proteins than its shorter partners. To remove the stop codon from DNA, a 3' primer lacking the stop codon is used during PCR construction. Constructs designed for prokaryotic *E. coli* display should incorporate sequences containing stem-loop structures at the 5' and 3' ends of the DNA to stabilise mRNA against degradation by RNase activities in *E. coli* cell-free systems.

The displayed polypeptide/protein can be a full length protein, or a fragment thereof, a protein domain, or a polypeptide, or a single chain antibody, and can be encoded by synthetic DNA.

One form of PRM complex is antibody-ribosome-mRNA (ARM) complex in which a single chain antibody protein-ribosome-mRNA complex is produced by in vitro translation. The single chain antibody protein can be full length or can be a binding fragment of a single chain antibody, a binding fragment is capable of binding a ligand. In antibody protein-ribosome-mRNA complexes, the single chain antibody can be, for example, a single-chain VH/K fragment in which the VH domain is linked to the complete light chain, i.e. VH-linker-VL-CL or a scFv fragment.

In a preferred embodiment, the ribosome display complex is treated before RT to reduce secondary structure and make mRNA accessible to primer(s), this may be carried out by heat and/or chemical treatment as described above.

Immediately prior to the RT step the mRNA ribosome complex is usually maintained at a temperature in the range of 4° C. to 10° C., generally at around 4° C. (e.g. on ice).

In methods where the association between the mRNA and protein in the ribosome display complex is maintained, so that the RT reaction is performed on mRNA associated with the complex, a heating step at a temperature in the range of 40° C.

to 70° C., preferably 42° C. to 65° C. was found to be useful prior to in situ RT to ensure full-length cDNA synthesis. If maintenance of the association between mRNA and protein in the ribosome complex is not a concern, pre-heating to a temperature in these ranges or higher than 65° C. can be used.

The temperature that can be used in the heating step is dictated by the mRNA secondary structure, which is determined by the mRNA sequence. The optimum temperature for a heating step for a given sequence can be readily determined experimentally, but temperatures in the range of 40° C. to 70° C., preferably 42° C. to 65° C., are generally suitable.

A method is provided for recovery of DNA fragments from mRNA in ribosome display complexes, said method comprising:

(a) heating of ribosome display complexes, followed by, (b) RT using a RT primer according to the invention which includes a sequence identical to or similar to the sequence at the 5' consensus region of the mRNA, followed by, (c) PCR using a single PCR primer according to the invention to amplify cDNA.

Also provided is a method for recovery of DNA fragments from mRNA in antibody ribosome mRNA (ARM) display complexes, said method comprising:

(a) heating of ARM complexes, followed by, (b) RT using a RT primer according to the invention which includes a sequence identical to or similar to the sequence at the 5' region of the mRNA, followed by, (c) PCR using a single PCR primer according to the invention to amplify cDNA.

In methods for recovery of DNA fragments from mRNA in ribosome display complexes or antibody ribosome display complexes, the PCR reaction may be performed on ss cDNA present either as mixture or a single molecule.

In methods for RT-PCR recovery of cDNA from mRNA in ribosome display complexes, it is preferred that the 5' region sequence of the RT primer is a sequence similar to or identical to the 5' region of the mRNA, including one or more of the sequences selected from the transcriptional start site, regulatory elements, kozak sequence, translational start codon, any part of the translated sequence or any family specific consensus sequence found in the 5' region.

In methods for RT-PCR recovery of cDNA from mRNA in ribosome display complexes, it is preferred that the single PCR primer used for PCR is identical or similar to or overlapping with, the 5' region sequence of the primer used for RT.

A preferred RT primer, suitable for use in methods of the invention that involve a RT reaction, is HuRT (SEQ ID NO:3)

A preferred single PCR primer, suitable for use in methods of the invention that include a PCR reaction, is Kz1 (SEQ ID NO: 1).

The design of the flanking sequence is based on a consensus sequence present in the 5' region of the mRNA population (FIG. 1). In the example described here, it is the sequence occurring from the start site of transcription to the translation initiation site (ATG). 5'-GAACAGACCACCATG-3' (SEQ ID NO: 1, KZ1 Primer). The hybridising sequence is based on a consensus sequence located at mRNA 3' region (FIG. 1) 5'-ACTTCGCA GGCGTAGAC-3' (SEQ ID NO: 2). Reverse transcription using the novel RT primer, comprising both the flanking sequence and the hybridising sequence in accordance with the invention (e.g. as shown in FIG. 1 as HuRT 5'-GMCAGACCACCATGACTTCGCAGGCGTAGAC-3' SEQ ID NO: 3), incorporates the flanking sequence into the single-stranded cDNA at both ends, allowing the resultant cDNA to be amplified by a single primer composed of the flanking sequence SEQ ID NO: 1 (FIG. 2). Single primer PCR avoids the need to optimise primer ratios and annealing temperatures, thus increasing PCR sensitivity and specificity with a wide choice of DNA polymerases. For recovering DNA such as from ribosome complexes, the introduction of the flanking sequence to the cDNA also distinguishes it from the original input DNA, eliminating any potential PCR amplification of the input template. Following this highly sensitive RT-PCR recovery, a second PCR is easily carried out using two primers to recreate a full-length DNA construct (FIG. 2). Such a construct obtained from cDNA of a ribosome display complex is suitable for subsequent cycles of ribosome display.

The main innovation is the novel design of an RT primer to incorporate a flanking sequence into single-stranded cDNA at both ends after ribosome display, making it possible to amplify the resultant cDNA by single primer PCR in a sensitive, specific and reproducible way. We have shown that the cDNA with a flanking sequence can be amplified up to 100 cycles without producing non-specific DNA bands or smearing. Thus, a single cDNA molecule can be efficiently amplified through 65 PCR cycles. To our knowledge, this is the first report of such a sensitive RT-PCR method for recovery of cDNA.

The methods of the invention can be fully or partially automated. Display of the mRNA protein complex can be automated, the RT reaction(s) can be automated and the PCR reaction(s) can be automated.

Using the present invention, it is possible to automate ribosome display, offering a powerful tool for simultaneously screening multi-display libraries or selection of different binders to various antigens.

The single primer PCR product can be easily converted into a suitable form for further manipulations such as protein expression in a cell-free system or in *E. coli*, or repeated cycles of ribosome display by a second PCR to introduce some necessary elements (e.g. T7 promoter, restriction enzyme sites, purification tag etc.) into the DNA construct.

Since this invention is capable of amplifying a single cDNA molecule, it is also possible to clone ds cDNA by PCR through ribosome display of functional proteins without using *E. coli* cells, providing a route to obtaining PCR clones through the encoded protein function. This in vitro PCR cloning would offer a number of advantages over *E. coli* cloning strategy in that (i) cDNA molecules are separated (e.g. by dilution) before they are amplified, so that individual cDNA species can be rapidly obtained by PCR, avoiding the time-consuming and laborious procedure of identifying *E. coli* clones after DNA amplification and cell transformation and (ii) it is possible to obtain individual DNA clones covering an entire cDNA population by high throughput PCR, whereas *E. coli* cloning generally only recovers a fraction of the population due to DNA manipulation and cell transformation, procedures resulting in loss of material.

In a method of the invention, separation of nucleic acid molecules, e.g. by dilution may be performed to provide a single, or small number of nucleic and molecules in each reaction. Thus, mRNA (either as free mRNA or in the form of a complex), may be diluted prior to the RT reaction. Dilution of the cDNA may be performed prior to the PCR reaction to provide a single or a small number e.g. 1, 2, 3, 4, 5 or 6, nucleic acid molecules per reaction. The single nucleic acid molecules and/or small groups of nucleic acid molecules can be produced by serial dilutions.

The invention is not restricted to the context of ribosome display systems, it has a broad application to recovery of cDNA from mRNA.

The present invention also provides kits for use in recovery of DNA. The kit comprises a supply of components for use in a method of this invention, and typically comprises a supply of a RT primer designed according to the invention, and one or more of a supply of dNTP, a supply of reverse transcriptase, a supply of ribonuclease inhibitor, buffer, RNase-free water. A kit according to the invention may also include PCR components such as DNA polymerase (e.g. Taq polymerase), PCR buffer(s), PCR primer(s) and dNTPs. The kits of this invention suitably include a set of instructions for use of the components in accordance with a method of this invention.

The present invention yet further provides a kit for a method of recovery of ss cDNA according to the invention, which comprises a supply of RT primer according to the invention, and one or more of a supply of dNTP, a supply of reverse transcriptase, a supply of ribonuclease inhibitor, buffer, RNase-free water.

The present invention yet further provides a kit for a method of recovery of ds cDNA according to the invention, which comprises a supply of single PCR primer according to the invention, preferably the single PCR primer comprises a 5' sequence based on the mRNA 5' region (which can be identical or similar to the mRNA 5'consensus region), and one or more of a supply of dNTP, a supply of reverse transcriptase, a supply of ribonuclease inhibitor, buffer, RNase-free water, supplemented with PCR components, such as DNA polymerase (e.g. Taq polymerase), PCR buffer(s), primers and dNTPs.

Lanes 1 and 2 show the results of the two tube PCR reaction, lanes 3 and 4 show the result of the one tube PCR reaction, lane 5 show a DNA size marker.

Figure 4:
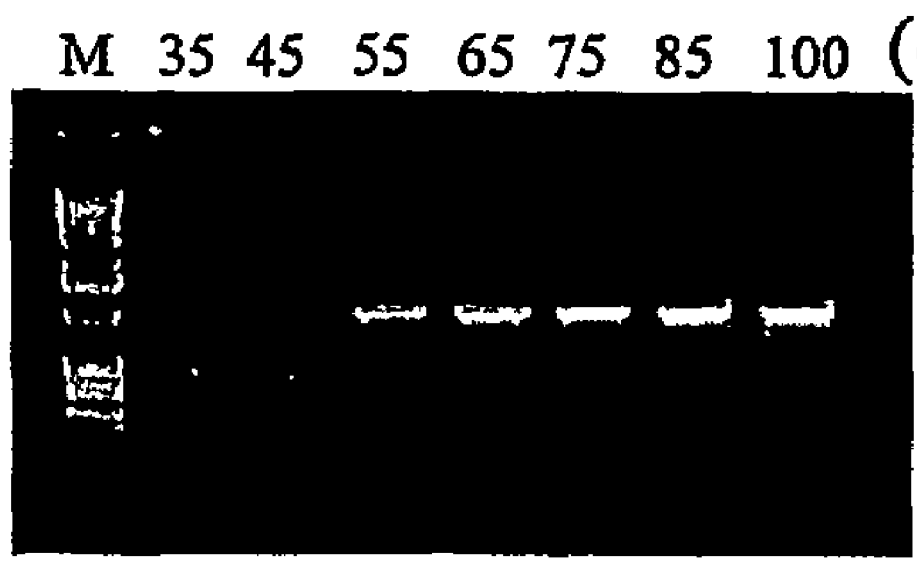

FIG. 4: Time course of 'single primer' PCR.

Lane 1 is a marker DNA, lane 2, 35 PCR cycles; lane 3, 45 PCR cycles; lane 4, 55 PCR cycles; lane 5, 65 PCR cycles; lane 6, 75 PCR cycles; lane 7, 85 PCR cycles; lane 8, 100 cycles.

Figure 5:
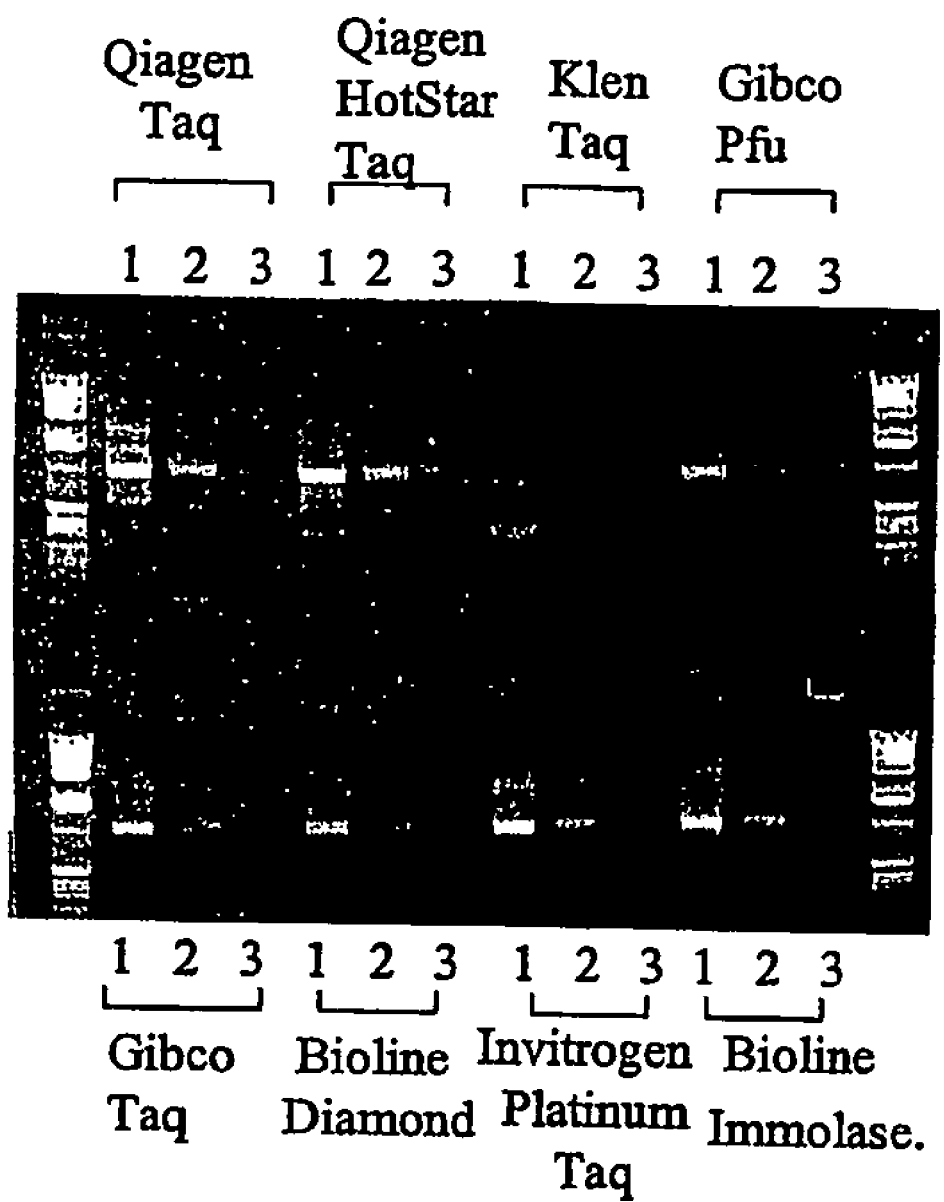

FIG. 5: Choice of PCR enzymes.

Figure 6:
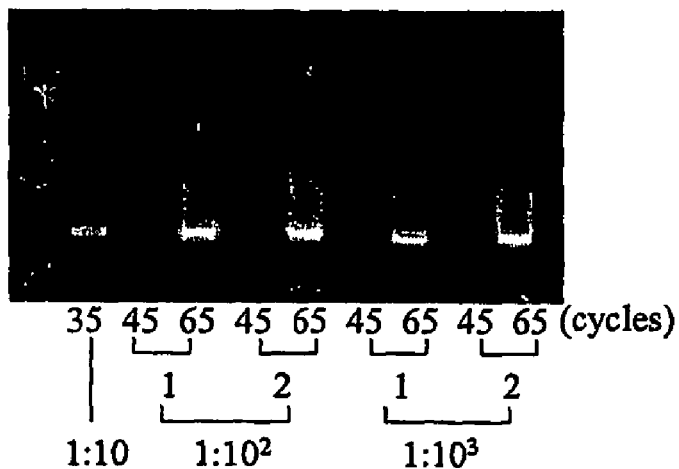
Figure 6:
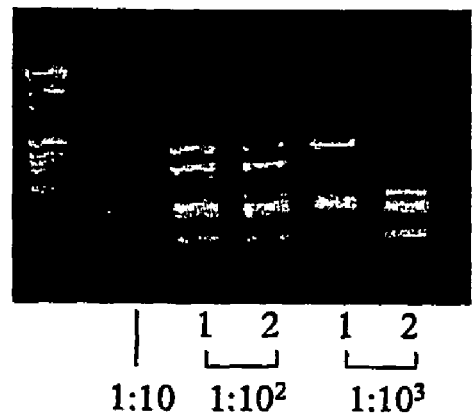

FIG. 6: PCR amplification of a single cDNA molecule (a) shows the results of single primer PCR, (b) shows the results of the fingerprinting experiments.

Figure 7:
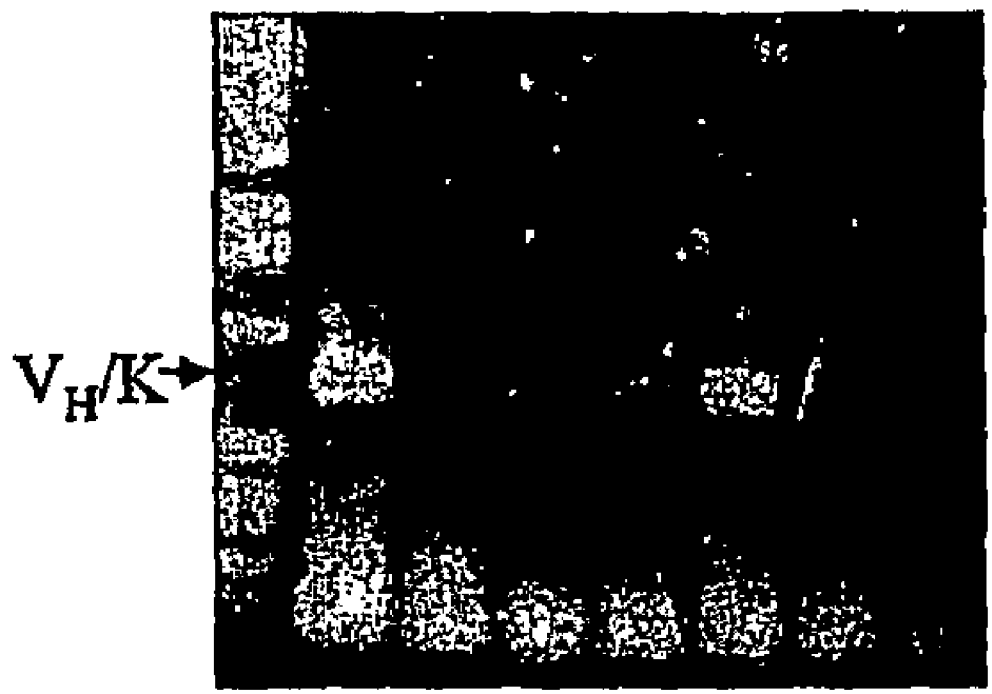

FIG. 7: Effect of pre-heating on DNA recovery efficiency.

Figure 8:
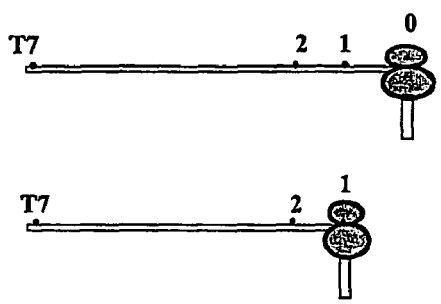
Figure 8:
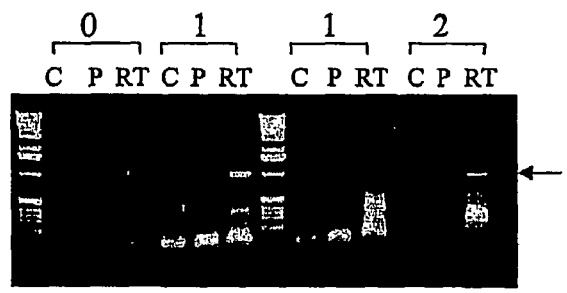

FIG. 8: Integrity of ARM complexes.

Figure 9:
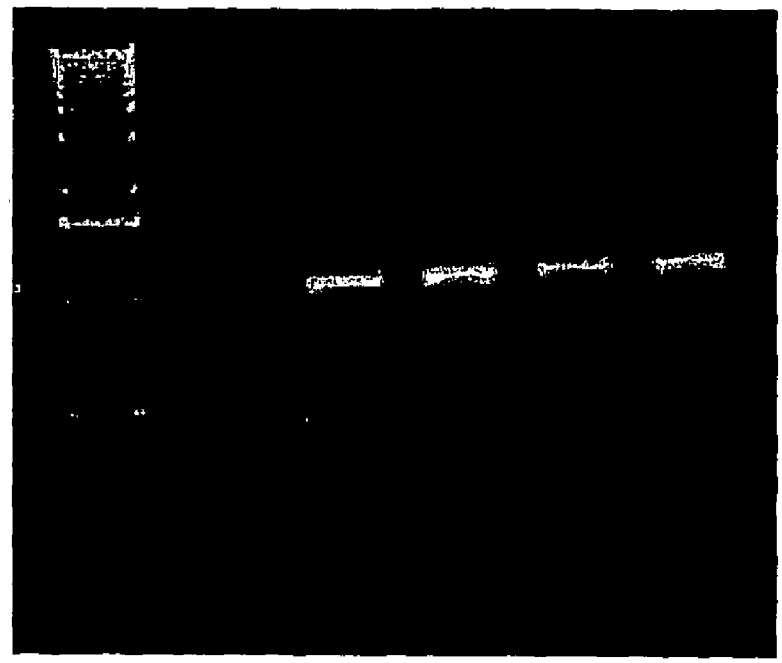

FIG. 9: Effect of pre-heating to 42° C. and 65° C. before RT step on DNA recovery efficiency.

EXAMPLES

1.0 RT-PCR Reaction 1.1 Materials:

Recovery from ribosome display is used as an example:

(1) Primers:
  (a) HuRT: 5'-<u>GAACAGACCACCATG</u>ACTTCGCAGG-CGTAGAC-3' is used for reverse transcription (SEQ ID NO: 3). The flanking sequence (SEQ ID NO: 1) is underlined.
  (b) Kz1: 5'-GMCAGACCACCATG-3' (SEQ ID NO: 1) is the flanking sequence and used for single primer PCR.

The following primers (c & d) are used for re-creation of the original full-length DNA construct for subsequent ribosome display cycles:

(c) T7 Ab:

(SEQ ID NO: 4)
5'-GGATCCTAATACGACTCACTATAGGGAACAGACCACCATG(C/G)

AGGT(G/C)CA(G/C)CTCGAG(C/G)AGTCTGG-3'.

The T7 promoter is indicated in bold.

(d) Hurex-Ck:

(SEQ ID NO: 5)
5'-CTCTAGAACACTCTCCCCTGTTGAAGCTCTTTGTGACGGGC

GAGCTCAGGCCCTGATGGGTGACTTCGCAGGCGTAGACTTTG-3'

(2). Enzymes:
  (a) ThermoScript (Invitrogen)
  (b) SuperScript™ II Rnase H⁻ Reverse transcriptase (Invitrogen)
  (c) SUPERase In (Ambion)
  (d) Taq DNA polymerases (Qiagen)

Figure 2:
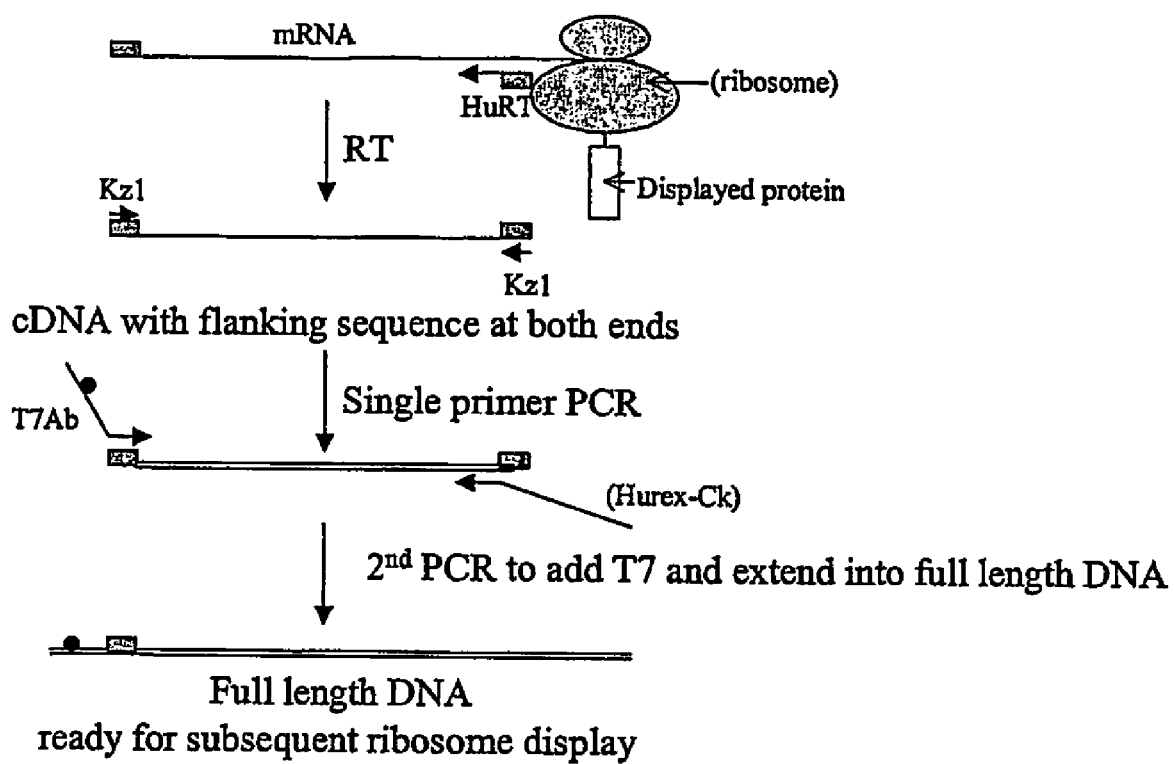
FIG. 2: The principle of the novel RT-PCR for cDNA recovery from ribosome complex.

1.2 Methods:

FIG. 2 shows the principle of the RT-PCR for DNA recovery from ribosome complexes. RT is first carried out on ribosome complexes without isolation of mRNA from the complexes using the primer HuRT (SEQ ID NO: 3). The resultant cDNA with the flanking sequence is then amplified by PCR using the primer Kz1 (SEQ ID NO: 1).

Ribosome-bound mRNA generated by ribosome display in the form of PRM complex is usually captured by a ligand-coated tubes or magnetic beads, washed five times with a cold (4° C.) washing buffer (PBS containing 5 mM Mg acetate and 0.1% Tween) (He et al., (1999) J. Immuno. Methods. 231: 105-117) and used for DNA recovery by the following procedure.

1.2.1 Reverse Transcription Reaction

To each sample, 12 μl of mixture containing 1 μl of 16 μM HuRT and 2 μl of 10 mM dNTP is added. The mixture is heated at 42° C. or 65° C. for 5 min, and then placed quickly on ice for at least 30 sec.

Reverse transcriptase is used to synthesise cDNA according to the manufacturer's instructions. The followings are two examples of the reverse transcription reaction:

(a) Using Thermoscript, 8 μl of mixture containing 4 μl of 5× cDNA synthesis buffer (included in the kit), 1 μl of 100 mM DTT, 1 μl of SUPERase In (20U), 1 μl of Thermoscript (15U) is added to the mixture from step 1 above and the incubation is carried out at 60° C. on a thermocycler for 45 min followed by 5 min at 85° C. Finally the mixture is held at 10° C.

(b) Using SuperScript™ II, 8 μl of mixture containing 4 ul of 5× First-Strand buffer (included in the kit), 1 ul of 100 mM DTT, 1 ul of SUPERase In (20U), 1 μl of Superscript™ II (200U) is added. The mixture is incubated at 42° C. for 45 min followed by 5 min at 85° C. Finally the mixture is held at 10° C.

The cDNA mixture produced is then transferred to a fresh tube for subsequent amplification by single primer PCR.

1.2.2 Single Primer PCR of Single-Stranded cDNA

Single primer PCR is carried out using a DNA polymerase according to manufacturer's instructions. The following PCR mixture is an example using Qiagen Taq polymerase.

| | |
|---|---|
| 10x buffer | 5 ul |
| 5xQ buffer | 10 ul |
| dNTPs (2.5 mM) | 4 ul |
| Primer Kz1 (8 uM) | 3 ul |
| Taq polymerase | 0.5 ul (2.5 units) |
| cDNA | 1-2 ul |
| $H_2O$ | to 50 ul |

Thermal cycling is carried out as follows: 35 cycles of 94° C. (1 min), 48° C. (1 min) and 72° C. (1.2 min), followed by one cycle at 72° C. for 8 min and finally placed on hold at 10° C.

The single primer PCR product is analysed and extracted from 1% agarose gel if necessary.

Figure 1:
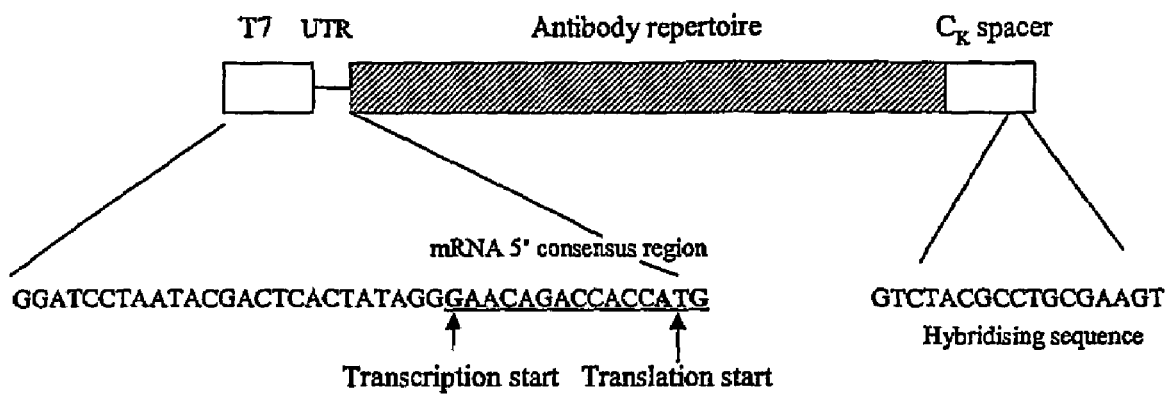
FIG. 1. DNA construct for the generation of ribosome display complex.

1.2.3 Conversion of Recovered DNA into a Suitable Construct for Subsequent Manipulations The following is an example of re-creating the full-length DNA construct for continuous ribosome display (see FIG. 1). The primers used are T7Ab (SEQ ID NO: 4) and Hurex-Ck (SEQ ID NO: 5) which contain T7 promoter and a part of the constant region for the extension of the construct into its original full-length (FIG. 1).

The ds cDNA is recovered by RT PCR. A second PCR procedure is carried out as follows:

| | |
|---|---|
| 10x buffer | 5 ul |
| 5 x Q buffer | 10 ul |
| dNTPs (2.5 mM) | 4 ul |
| T7Ab (16 uM) | 1.5 ul |
| Hurex-Ck (16 uM) | 1.5 ul |
| Gel-purified DNA fragment | 50-100 ng |
| Taq polymerase (Qiagen) | 0.5 ul (2.5 units) |
| $H_2O$ | to 50 ul |

Thermal cycling is carried out by 20-30 cycles of 94° C. (1 min), 60° C. (1 min) and 72° C. (1.2 min), followed by 72° C. for 8 min and finally placed on hold at 10° C.

After agarose gel analysis, the PCR product is ready for ribosome display.

1.2.4 The Novel RT-PCR is More Effective in the Two-Tube Format

Figure 3:
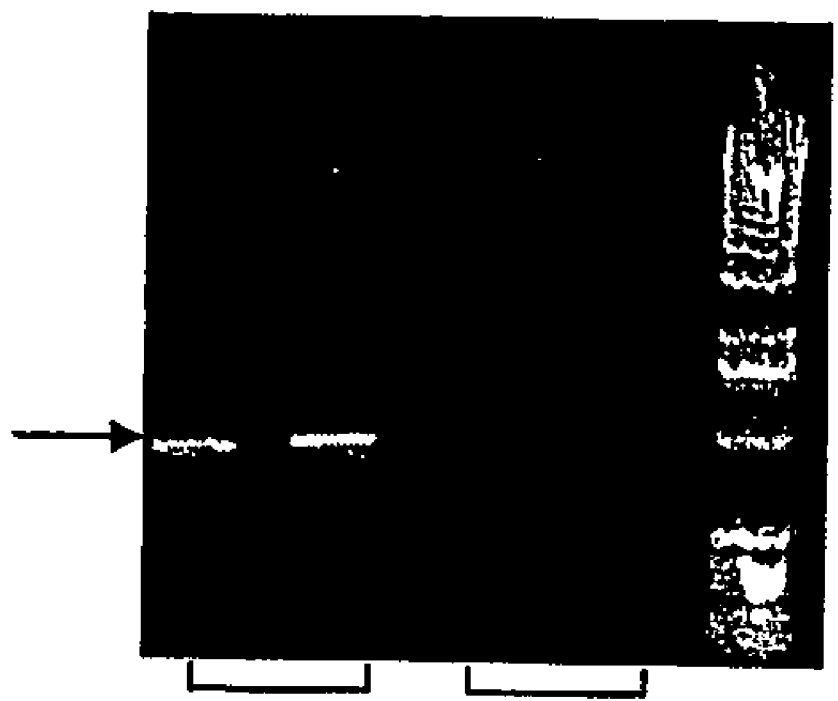
FIG. 3: Efficiency of two-tube RT-PCR.

DNA recovery efficiency was compared using the invented RT-PCR in either two-tube or one-tube formats. Commercially available one-tube RT-PCR kit and two tube RT-PCR systems from Invitrogen were chosen as they use the same enzymes. Antibody-ribosome-mRNA (ARM) complexes captured by carcinoembryonic antigen (CEA) after ribosome display were subjected to RT-PCR using the two systems side by side with identical primers. Analysis of the RT-PCR products showed that while one tube RT-PCR produced no DNA in this case, the two-tube system generated very strong DNA recovery (FIG. 3), demonstrating that the invented RT-PCR procedure is more effective in two-tube format.

1.2.5 Single Primer PCR Efficiently and Specifically Amplifies cDNA with the Flanking Sequence.

The sensitivity and specificity of the single primer PCR for amplification of cDNA with the flanking sequence was tested by carrying out a time course of 100 PCR cycles. In this experiment, cDNA generated after RT was diluted 1000 times and PCR was carried out as in total volume of 200 μl. During PCR cycles, 20 μl samples were taken at the following points: 35 cycles, 45 cycles, 55 cycles, 65 cycles, 75 cycles, 85 cycles and 100 cycles. Gel analysis of PCR product showed that a single DNA fragment was specifically amplified up to 100 cycles without detection of DNA smearing or additional products (FIG. 4).

1.2.6 Single Primer PCR Works with Wide Choice of DNA Polymerases.

A variety of DNA polymerases from different commercial companies including Qiagen, KlenTaq, Gibco, Bioline and Invitrogen were tested for the single primer PCR. FIG. 5 showed that most Taq polymerases and proofreading enzymes amplify the resultant cDNA very effectively, indicating that the invented single primer PCR method is suitable for use with a wide range of DNA polymerases without the need for optimisation.

1.2.7 Single Primer PCR is Capable of Amplifying Single cDNA Molecules

To see whether a single cDNA molecule can be recovered by single primer PCR from a cDNA mixture generated by ribosome display, a naïve human antibody library was subjected to ribosome display and BSA selection. After RT, the resultant cDNA was first quantified by PCR comparison with a known amount of template. This gave an indication that the cDNA concentration obtained was 10 fg/ul (equivalent to 1000 molecules, data not shown). The cDNA was then serially diluted to a point where it contained no more than one molecule per 1 μl. This was tested by PCR of serial dilutions (1:10, $1:10^2$, $1:10^3$ and $1:10^4$), showing that no PCR product was detected in the dilution of $1:10^4$ in 80 cycles and only half of samples from $1:10^3$ dilution produced PCR product, suggesting cDNA concentration of no more than one molecule/1 ul was produced in the $1:10^3$ dilution (data not shown). In order to test if single cDNA molecules could be recovered by PCR from the $1:10^3$ dilution, DNA fingerprinting by MvaI restriction and direct DNA sequencing were used. FIG. 6a showed while a 1:10 dilution produced a $V_H$/K band by 35 PCR cycles, templates from $1:10^2$ and $1:10^3$ dilutions required 65 cycles to reveal the band. DNA fingerprinting revealed that whereas PCR fragment from 1:10 and $1:10^2$ dilution gave a similar digestion pattern, the templates from $1:10^3$ produced different DNA patterns among the duplicates (FIG. 6b), suggesting a single cDNA was amplified from $1:10^3$ dilution. Direct DNA sequencing of the PCR fragments from $1:10^3$ dilution showed only one unique sequence from each sample, further confirming the recovery of individual cDNA molecules by single primer PCR.

1.2.8 Pre-Heating Ribosome Display Complexes at 65° C. Improves the Synthesis of Full-Length cDNA Heating of ribosome ARM complexes (e.g. at 65° C.) prior to RT was found to improve the recovery of full-length cDNA. FIG. 7a shows a comparison of RT-PCR with or without a pre-heating step at 65° C. In this experiment, ARM complexes were selected by CEA. After the final wash with ice-cold water (He et al., (1999) J. Immuno. Methods. 231: 105-117), the ARM complexes were treated either by heating at 65° C. for 5 min or without the pre-heating step, followed by cDNA synthesis at 60° C. using ThermoScript (Invitrogen). This showed that about 10 fold more $V_H$/K DNA was recovered from the pre-heated sample. Samples without pre-heating gave very poor DNA detection even at optimised temperatures (50° C. to 60° C.) for the activity of Thermo-Script (FIG. 7).

1.2.9 The Ribosome Complex Remains Intact at 65° C.

The integrity of ARM complexes at the elevated temperature during the heating step was tested by reverse transcription of the ribosome-attached mRNA with primer 1, which anneals at about 100 bp upstream of the stalled ribosome complex (FIG. 8a) and with primer 0 which anneals at the 3' region of mRNA covered by the stalled ribosome. The RT process was carried out as described above using Thermoscript. While little or no PCR products were observed with primer 0, which is blocked in an intact complex (FIG. 8b, lane 4), the full-length product was generated with the upstream primer 1 (FIG. 8b, lane 7). A PCR template terminating at the primer 1 site that worked in the first round was then employed (FIG. 8a). Again, while the 3' terminal primer 1 did not produce full-length PCR product (FIG. 8b lane 11), an upstream primer 2 was successful (lane 14). This showed that the 3'end of the mRNA was inaccessible to a primer, probably due to the occupancy of a stalled ribosome under the RT conditions. This suggests that ribosome complexes remained intact after pre-heating at 65° C.

1.2.10 Performing the Reverse Transcription Reaction on ARM Complexes After Using a 42° C. or 65° C. Heating Step The effect of a heating step at 42° C. on DNA recovery was tested using SuperScript™ II (Invitrogen). In this experiment, anti-progesterone ARM complexes were generated and captured by two separated tubes pre-coated with progesterone. After the final wash with a cold water as described (He et al., (1999) J. Immuno. Methods. 231: 105-117), one of the tubes was subjected to 42° C. for 5 min. The other tube was heat treated at 65° C. for 5 min as described above. RT reactions were then performed at 42° C. for 45 min in parallel followed by PCR using the single primer procedure for 35 cycles.

The PCR product was analysed on an agarose gel, this showed that a similar DNA level was recovered from both 42° C. and 65° C. treatments (FIG. 9). This suggests that the RT reaction can be carried out using a pre-heating step at 42° C. and using Superscript™ II.

Example 2

Automation of the Method

Ribosome display can performed by the following procedure using a robot such as Tecan miniprep 75. To each well of a microtitre plate, 10 ul of PCR library is added, this is followed by addition of 40 ul of TNT mixture containing 0.02 mM methionine and 1 mM Mg acetate; incubation is performed at 30° C. for 1 hr; then to each well is added 20 ul of a mixture containing 7 μl of 10× DNase I buffer and 100U DNase I. The reaction mixture is incubated at 30° C. for 20 min; then 70 μl of cold 2× dilution buffer is added to each well. The mixture (140 ul) is then transferred to the wells of Nucleolink™ strips (NUNC) coated with ligand(s) and incubated at 4° C. for 2 hrs, with gentle shaking, to permit binding of the PRM complex with the immobilised ligand. The wells are then washes 5 times using washing buffer, then two times using sterile distilled H$_2$O.

For the reverse transcription reaction, 12 ul of reverse transcription mix 1 is added to each well and incubation is performed at 65° C. for 5 min, then on ice for 1 min. Next 8 ul of RT mix 2 is added to each well and incubation performed at 60° C. for 45 min followed by 85° C. for 5 min.

The resultant cDNA can be amplified by PCR either as a pooled template for further ribosome display cycles (by repeating ribosome display procedure above), or can be subjected to in vitro PCR cloning.

For in vitro PCR cloning, the cDNA molecules are divided by serial dilution into samples containing a single molecule or small number of molecules in microtitre wells. Amplification of the cDNA dilution is performed using single primer PCR as described above and thermo-cycling on PTC200 (MJ Research) for 35-65 cycles A sample of the PCR product can be analysed by restriction digestion and agarose gel electrophoresis and visualisation. The PCR product can be subjected to PCR assembly by mixing individual PCR fragments with a plasmid containing essential elements for cell free expression (He and Taussig, 2001) the reaction being performed by thermo-cycling as above. The assembled PCR product can be analysed, e.g. by restriction enzyme digestion, agarose gel electrophoresis and visualisation of the DNA bands.

```
Sequence listing information
SEQ ID NO: 1
5'-GAACAGACCACCATG-3'
KZ1 Primer flanking sequence.

SEQ ID NO: 2
5'-ACTTCGCAGGCGTAGAC-3'
Hybridising sequence is based on a consensus se-
quence located at mRNA 3'
region SEQ ID NO: 3
5'-GAACAGACCACCATGACTTCGCAGGCGTAGAC-3'
HuRT, a RT primer in accordance with the inven-
tion, comprising both the flanking sequence KZ1
(SEQ ID NO: 1) and the hybridising sequence
(SEQ ID NO 2).

SEQ ID NO: 4
5'-
GGATCCTAATACGACTCACTATAGGGAACAGACCACCATG(C/
G)AGGT(G/C)CA (G/C)CTCGAG(C/G)AGTCTGG-3'
T7Ab, the T7 promoter is indicated in bold.

SEQ ID NO: 5
5'-
CTCTAGAACACTCTCCCCTGTTGAAGCTCTTTGTGACGGGCGAGCTCAG
GCC CTGATGGGTGACTTCGCAGGCGTAGACTTTG-3'

Hurex-Ck.

<110> Discerna Ltd

<120> Recovery of DNA

<130> WPP290012

<150> GB0306305.4

<150> GB0311351.11

<151> 2003-03-19

<160> 5

<170> PatentIn version 3.1

<210> 1

<211> 15

<212> DNA

<213> Artificial

<400> 1
gaacagacca ccatg                                              15

<210> 2

<211> 17

<212> DNA

<213> Artificial

<400> 2
```

-continued acttcgcagg cgtagac                                        17

<210> 3
<211> 32
<212> DNA
<213> Artificial
<400> 3
gaacagacca ccatgacttc gcaggcgtag ac                       32

<210> 4
<211> 63
<212> DNA
<213> Artificial

<400> 4
ggatcctaat acgactcact atagggaaca gaccaccatg               60
saggtscasc tcgagsagtc
tgg                                                       63

<210> 5
<211> 83
<212> DNA
<213> Artificial
<400> 5
ctctagaaca ctctcccctg ttgaagctct ttgtgacggg               60
cgagctcagg ccctgatggg
                                                          83
tgacttcgca ggcgtagact ttg

---

SEQUENCE LISTING

<160> NUMBER OF SEQ ID NOS: 5

<210> SEQ ID NO 1
<211> LENGTH: 15
<212> TYPE: DNA
<213> ORGANISM: Artificial sequence
<220> FEATURE:
<223> OTHER INFORMATION: KZ1 primer flanking sequence

<400> SEQUENCE: 1
gaacagacca ccatg                                          15

<210> SEQ ID NO 2
<211> LENGTH: 17
<212> TYPE: DNA
<213> ORGANISM: Artificial Sequence
<220> FEATURE:
<223> OTHER INFORMATION: Hybridising sequence based on a consensus
      sequence located at the mRNA 3' region

<400> SEQUENCE: 2
acttcgcagg cgtagac                                        17

<210> SEQ ID NO 3
<211> LENGTH: 32
<212> TYPE: DNA
<213> ORGANISM: Artificial Sequence
<220> FEATURE:
<223> OTHER INFORMATION: HuRT primer, a RT primer comprising both the
      flanking sequence K Z1 (SEQ ID NO: 1) and the Hybridising sequence
      (SEQ ID NO: 2).

<400> SEQUENCE: 3
gaacagacca ccatgacttc gcaggcgtag ac                       32

<210> SEQ ID NO 4
<211> LENGTH: 63
<212> TYPE: DNA
<213> ORGANISM: Artificial Sequence
<220> FEATURE:
<223> OTHER INFORMATION: T7Ab sequence, including the T7 promoter
      sequence

```
<400> SEQUENCE: 4
ggatcctaat acgactcact atagggaaca gaccaccatg saggtscasc tcgagsagtc      60
tgg                                                                    63

<210> SEQ ID NO 5
<211> LENGTH: 83
<212> TYPE: DNA
<213> ORGANISM: Artificial Sequence
<220> FEATURE:
<223> OTHER INFORMATION: Hurex-Ck sequence

<400> SEQUENCE: 5
ctctagaaca ctctcccctg ttgaagctct ttgtgacggg cgagctcagg ccctgatggg      60
tgacttcgca ggcgtagact ttg                                              83
```

The invention claimed is:

1. A method for RT-PCR recovery of cDNA from mRNA in ribosome display complexes, said method comprising:

(a) reverse transcribing mRNA in ribosome display complexes or isolated from ribosome display complexes using an RT primer comprising a 5' sequence which is identical to a 5' consensus region of the mRNA or which has at least 80% homology to the 5' consensus region of the mRNA and is capable of hybridizing specifically with DNA complementary to a part of the mRNA 5'region in the conditions under which the reverse transcription step is performed and comprising a 3' primer region sequence complementary to a 3' region of the mRNA, whereby single stranded cDNA is generated; and (b) amplifying by PCR the single stranded cDNA using a single type of primer which is identical to or overlapping with the 5' sequence of the RT primer used, or which has at least 80% homology to the 5'consensus region of the mRNA and is capable of hybridizing specifically with DNA complementary to a part of the mRNA 5' region in the conditions under which the reaction is performed.

2. The method according to claim 1 wherein in step (b), the single stranded cDNA is present as a mixture or a single type of cDNA molecule.

3. The method according to claim 1, wherein the ribosome display complexes are treated before step (a) to make the mRNA accessible to one or more primers, optionally by at least one of heating and a chemical method.

4. A method for recovery of DNA fragments from mRNA in ribosome display complexes, said method comprising:

(a) heating of ribosome display complexes, followed by, (b) reverse transcribing mRNA in ribosome display complexes or isolated from ribosome display complexes using an RT primer comprising a sequence identical to a sequence at a 5' consensus region of the mRNA, or which has at least 80% homology to the 5'consensus region of the mRNA and is capable of hybridizing specifically with DNA complementary to a part of the mRNA 5'region in the conditions under which the reverse transcription step is performed, whereby single stranded cDNA is generated; and (c) amplifying by PCR the single stranded cDNA using a single type of primer which is identical to or overlapping with the 5' sequence of the RT primer used, or which has at least 80% homology to the 5'consensus region of the mRNA and is capable of hybridising specifically with DNA complementary to a part of the mRNA 5' region in the conditions under which the reaction is performed.

5. The method according to claim 4 wherein in step (c) the single stranded cDNA is present as a mixture or a single type of cDNA molecule.

6. The method according to claim 1 or 4, wherein the ribosome display complex is an antibody-ribosome-mRNA complex.

7. The method according to claim 1 or 4, wherein the RT primer comprises a 5' region comprising one or more sequences selected from the group consisting of a transcriptional start site, a regulatory element, a kozak sequence, a translational start codon, any part of a translated sequence, and any family specific consensus sequence found in the 5' region.

8. The method according to claim 1 or 4, wherein the RT primer comprises HuRT (SEQ ID NO: 3).

9. The method according to claim 1 or 4, wherein the single type of primer comprises Kz1 (SEQ ID NO: 1).

10. The method according to claim 1, wherein the ribosome display complexes are treated before step (a) to make mRNA accessible to one or more primers, by heating, or by a chemical method, or by heating and a chemical method.

\* \* \* \* \*